United States Patent [19]

Miller

[11] 3,931,650

[45] Jan. 13, 1976

[54] DISPOSAL DEVICE FOR WHEELCHAIRS

[76] Inventor: Kent A. Miller, 7775 La Costa Circle, Buena Park, Calif. 90620

[22] Filed: Mar. 24, 1975

[21] Appl. No.: 561,258

Related U.S. Application Data

[63] Continuation-in-part of Ser. No. 382,580, July 25, 1973, abandoned.

[52] U.S. Cl. ............................ 4/134; 4/254; 5/90; 297/188; 297/192; 297/DIG. 4
[51] Int. Cl.² .................... A47K 11/02; A47K 7/02
[58] Field of Search ............ 4/1, 134, 112, 90, 110; 5/90; 297/DIG. 4, 188, 192, 180; 128/295, 275

[56] References Cited
UNITED STATES PATENTS

| | | | |
|---|---|---|---|
| 559,109 | 4/1896 | Stoltz | 4/134 |
| 1,322,421 | 11/1919 | French | 4/110 |
| 1,869,036 | 7/1932 | Zink | 5/90 |
| 2,086,550 | 7/1937 | Hartig | 4/134 |
| 3,038,174 | 6/1962 | Brown et al. | 5/90 X |
| 3,415,299 | 12/1968 | Hinman, Jr. et al. | 4/110 X |
| 3,564,620 | 2/1971 | Clark | 4/110 |
| 3,787,903 | 1/1974 | Miller | 4/134 |

*Primary Examiner*—Henry K. Artis
*Attorney, Agent, or Firm*—Knobbe, Martens, Olson, Hubbard & Bear

[57] ABSTRACT

A urine collection container carried by a person confined to a wheelchair includes a drain tube which is connected to a valve mounted on the person's wheelchair to permit the person, unattended, to empty the contents of the collection container onto the ground or into a floor drain beneath the wheelchair. The valve may be manually operated, as by a lever within reach of the wheelchair occupant, or may be operated using a solenoid. The latter construction permits remote operation of the valve utilizing a low current sensitive switch operable, for example, by a quadraplegic. In addition, the solenoid operated valve permits the use of a timing circuit which automatically closes the valve a predetermined period of time after the valve is open to prohibit the valve from accidentally being left open and additionally to permit handicapped persons to both open and close the valve with a single switch operation.

6 Claims, 8 Drawing Figures

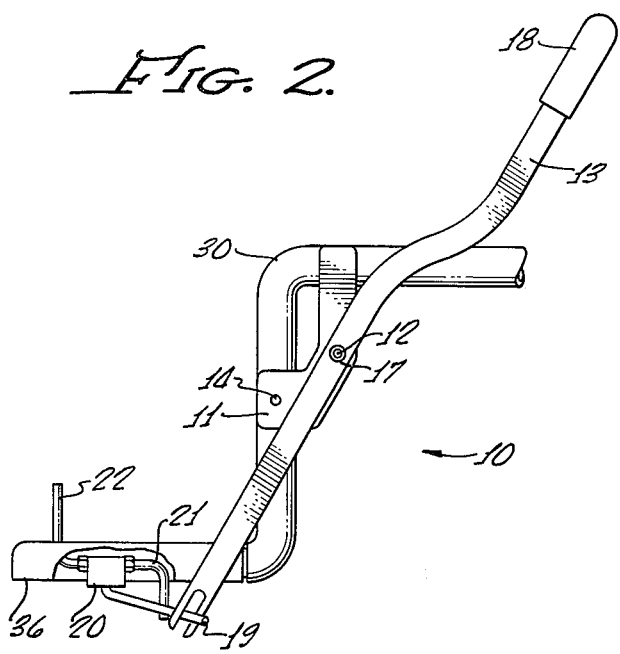
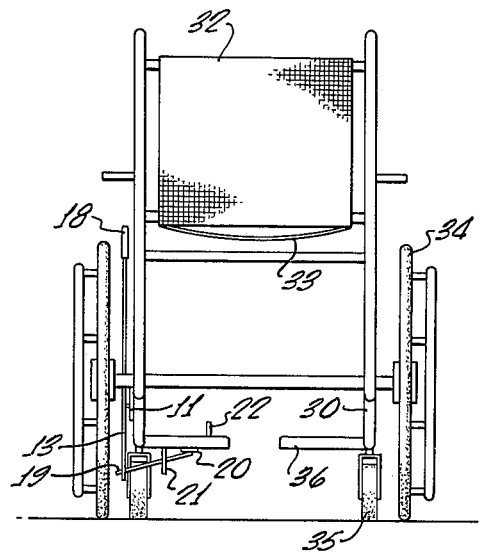
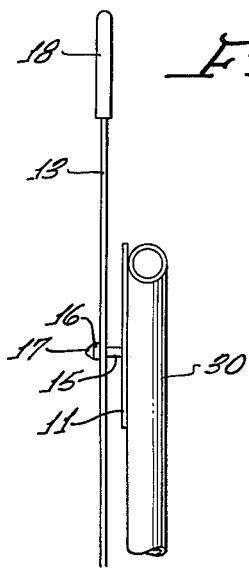
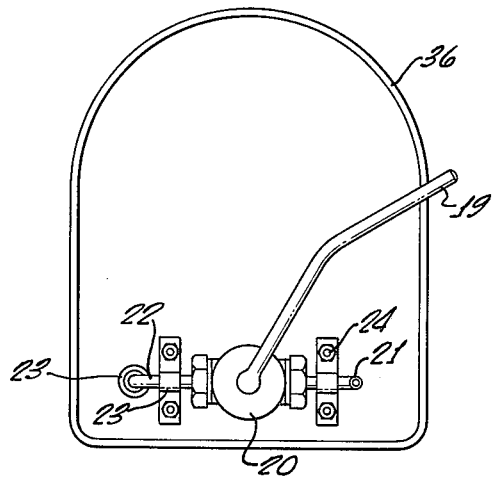

DISPOSAL DEVICE FOR WHEELCHAIRS

RELATED APPLICATION

This application is a continuation-in-part of copending application Ser. No. 382,580, filed July 25, 1973 entitled Disposal Device For Wheel Chairs and now abandoned.

BACKGROUND OF THE INVENTION

This invention relates to urine collection containers, and specifically to leg bags which are utilized by persons confined to wheelchairs, for the collection of urine. More particularly, this invention relates to a valve device connected to the drain opening of such a bag and adapted to open and close the bag drain to permit the contents of the bag to be dumped onto the ground or into a floor drain over which the wheelchair is positioned.

In the conventional drainage bag, a drain tube is connected to the bag to permit emptying. This is a frequent requirement, because paraplegic or quadraplegic patients excrete exceptional amounts of urinary waste to compensate for deficiencies in other excretory processes. Particularly for quadraplegic and paraplegic patients, this operation requires the assistance of an attendant and thus reduces the independence of the patient and may at times cause embarrassment for the patient.

Prior to the present invention, apparatus did not exist which would allow a person confined to a wheelchair and utilizing a urine collection bag or leg bag to conveniently empty the contents of the bag below the wheelchair without the assistance of an attendant. In addition, it has been virtually impossible for paraplegics or quadraplegics to remain unattended for a substantial period of time because of the need for frequent emptying of the leg bag.

SUMMARY OF THE INVENTION

The present invention utilizes a valve which is permanently attached to the wheelchair of the patient, typically a quadraplegic or paraplegic. The valve is connected by tubing to the patient's leg bag and the outlet of the valve is connected, preferably through rigid tubing, to a point beneath the wheelchair. This latter outlet tubing is situated on the wheelchair in a position which permits the tubing to be placed over a floor drain, for example, so that the patient can move the wheelchair to a position above the floor drain and empty the contents of the leg bag without assistance.

Furthermore, the present invention contemplates not only a mechanical valve actuator usable by patients who have the use of their arms, but in addition contemplates the use of a solenoid valve operable by quadraplegics. In this latter instance, the solenoid valve is conveniently connected to a power source, such as a storage battery, through an electronic circuit which permits the use of a control switch which carries extremely low current. The reduction in current through the control switch permits the use of sensitive switches, such as tongue operated switches, operable by a quadraplegic, without a risk of electrical shock or fire.

In addition, the invention contemplates an electronic circuit for controlling solenoid operation which permits a sensitive switch such as a tongue switch to open the solenoid valve and which closes the solenoid valve automatically a predetermined time after opening in order to assure that the valve is not inadvertently left open. The apparatus thus avoids possible embarrassment to the patient and, in addition, permits a single operation of the sensitive switch, such as a tongue switch, to both open and close the valve.

These and other advantages of the present invention are best understood through a reference to the drawings, in which:

FIG. 1 is a rear elevation view of a wheelchair including the mechanical assembly of the mechanically operated valve of the present invention;

FIG. 2 is a side elevation view of the mechanical valve actuator assembly of the present invention, partially broken away from the wheelchair;

FIG. 3 is a rear elevation view of the mechanical assembly of FIG. 2, broken away from the wheelchair;

FIG. 4 is a bottom plan view of the valve of FIGS. 1 and 2 and the mounting thereof to the footrest of the wheelchair;

DETAILED DESCRIPTION OF THE PREFERRED EMBODIMENT

Figure 5:
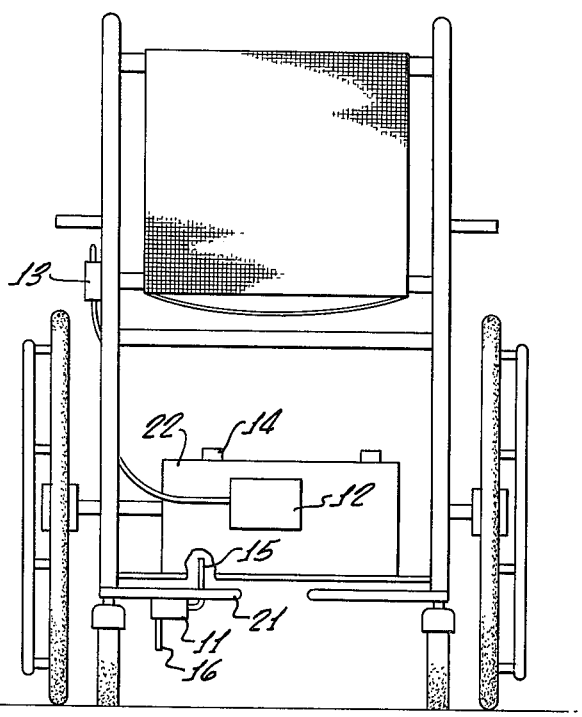
FIG. 5 is a rear elevation view of a wheelchair similar to the wheelchair of FIG. 1 equipped with the electrical solenoid valve and control circuit of the present invention.

Referring initially to FIGS. 1 through 4, the overall mechanical valve and control assembly is designated by the numeral 10. This apparatus is secured to an invalid wheelchair which includes a support frame 30, a back 32, a seat 33, a pair of rear wheels 34, a pair of front directional wheels 35, and a pair of foot support pedals 36. In addition to the elements shown in FIG. 1, the invalid wheelchair may typically include an electric storage battery and motor means for auto-propulsion, as is well known in the wheelchair art.

When a patient is situated on the seat 33, the flexible outlet or drain tube from his collection bag may conveniently be attached onto an upstanding tube 22 which, as shown in FIGS. 1, 2 and 4, is connected to the inlet of a manually actuated valve 20 and may conveniently pass through an opening in the footrest 36. If the outlet tube from the collection bag has a mechanical valve, such as a pinch valve which pinches the tubing to prohibit fluid flow, this valve is opened after the tube is connected to the upstanding tube 22 so that fluid communication exists between the collection bag and the valve 20. The valve 20 additionally includes an outlet tube 21 which is typically constructed of metal and is directed downward from the valve 20. This tube 21 projects below the footrest 36 a sufficient distance so that relatively inconspicuous disposal of the leg bag contents through the valve 20 and the tube 21 may occur. The placement of the outlet tube 21 beneath the footrest 36 is convenient since it enables the wheelchair occupant to position the tube 21 above a floor drain or other receptacle so that the leg bag contents may be disposed of.

The assembly of the valve 20 and the metal tube sections 21 and 22 is secured to the lower surface of the foot support pedal 36 by means of two clamps 23 which are secured, in turn, to the foot support pedal 36 by means of machine screws, nuts and washers 24. Alternatively, the valve 20 may be secured to the foot support pedal 36 through the use of machine screws passing through the foot support pedal 36 into tapped holes in the body of the valve 20.

From the above description it can be seen that the valve 20 is normally closed and prohibits flow of fluid from the leg bag onto the floor or ground beneath the wheelchair. When the valve 20 is opened by manipulation of a rotating valve arm 19, fluid flows from the leg bag out of the outlet tube 21 onto the ground or into a drain. This rotating valve arm 19 is manipulated by the apparatus shown in detail in FIGS. 2 and 3.

A support plate 11 is securely fastened to the support frame 30 either through a weldment to the support frame or by means of machine screws passing through the support plate 11 and the support frame 30. The support plate 11 includes a pivot pin 12 projecting therefrom to support an elongate lever 13 and, in addition, includes a projecting stop pin 14 to limit the movement of the lower part of the lever 13 in the forward direction. The lever 13 may be spaced from the support plate 11 by a spacer 15 to prevent striking of the lever 13 against the support frame 30, and a washer 16 and retaining tap nut 17 is used to secure the lever 13 to the pivot pin 12. The upper end of the lever 13 is long enough to permit actuation of the lever 13 by means of friction of the patient's arm against a rounded protective knob 18 covering the upper end of the lever 13. During actuation, the lever 13 is rotated in a clockwise direction about the pivot pin 12, as viewed in FIG. 2.

The lower end of the lever 13 includes a notch into which is engaged the valve arm 19. Thus, rotation of the lever 13 about the pin 12 rotates the valve arm 19, so that the valve 20 is opened when the lever 13 contacts the stop pin 14. The notched configuration of the lever 13 additionally permits rotation of the foot support pedal 36 into an upright position, with a resulting rotation of the valve 20 and valve arm 19 out of engagement with the notch on the lever 13.

In using the device illustrated in FIGS. 1 through 4, the occupant of the wheelchair moves the wheelchair above a floor drain or other location where the collection bag is to be emptied. He then manipulates the lever 13 to open the valve 20, permitting flow of fluid from the collection bag onto the ground. When the bag is empty, the lever 13 is again manipulated, this time in a counter-clockwise direction as viewed in FIG. 2, to close the valve 20.

Figure 6:
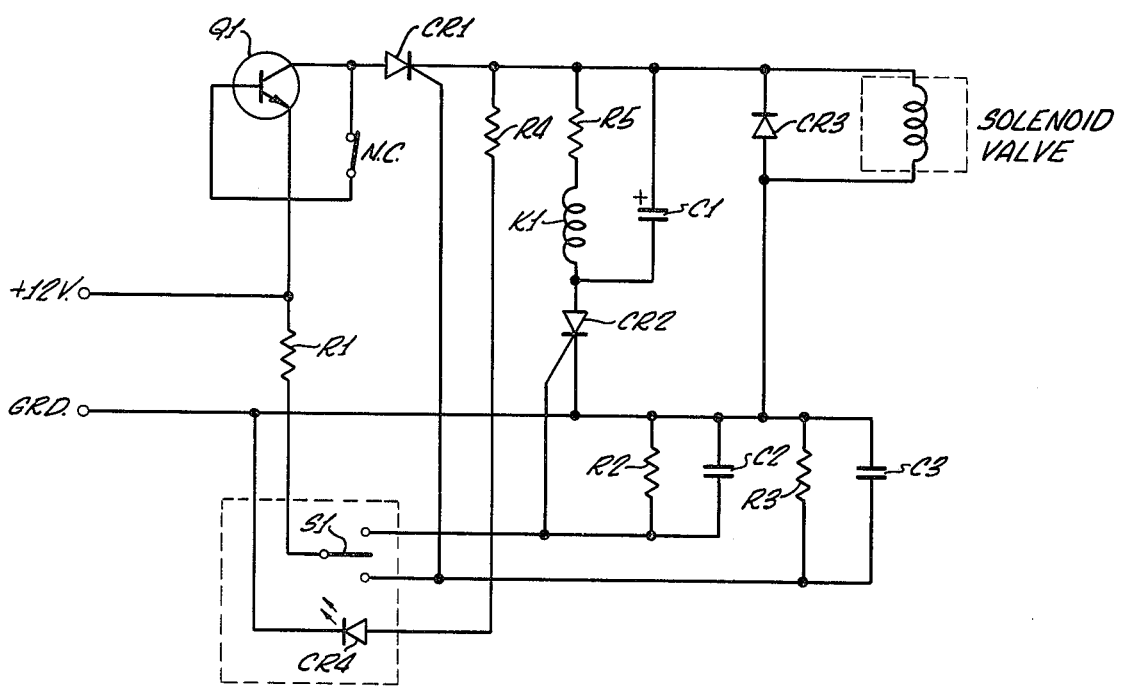
FIG. 6 is a schematic illustration of the electrical circuit utilized for controlling the solenoid valve of the apparatus shown in FIG. 5.

Referring now to FIGS. 5 and 6, an alternate embodiment of the present invention, utilizing an electrical solenoid valve for controlling fluid flow from the patient's leg bag, will be described. In this instance, the apparatus is connected to a wheelchair identical to the wheelchair shown in FIG. 1 and identified by like numerals. The disposal apparatus includes a solenoid valve 37 which is secured to the footrest 36 of the wheelchair, and is electrically connected to a source of electrical current, such as a storage battery 39, through a control circuit 41. The control circuit 41 may conveniently be attached to the storage battery 39. In addition, this control circuit 41 is connected electrically to a switch 43 which, in the embodiment shown in FIG. 5, is a toggle switch mounted proximate the wheelchair occupant to permit manipulation by the occupant's arm or hand. Alternatively, the circuit 41 may be mounted as a unit with the switch 43, both being within reach of the occupant. In an alternate construction, a well known tongue-activated switch, or other switches designed for manipulation by different portions of a paraplegic's or quadraplegic's body, may be used to replace the switch 43. In each instance, it will be understood that the particular switch 43 is selected for the convenience of the wheelchair occupant.

The electrical components which make up the solenoid valve 37, control circuit 41, and switch 43 are shown schematically in FIG. 6. The purpose of the control circuit 41 is to permit operation of the electrical solenoid 37, which requires relatively high current, under the control of a low current switch 43. The control circuit 41 thus substantially reduces the danger of electrical shock or fire at the location of the switch 43 and permits, for example, a tongue-operated switch without hazard to the wheelchair occupant. As in the previous embodiment of FIGS. 1 through 4, operation of the solenoid valve 37 permits flow of urine from the patient's leg collection bag through a flexible tube which is connected onto an inlet valve tube 22, through the solenoid valve 37, and out of an exit tube 21 beneath the wheelchair. In many instances, the storage battery 39 utilized to operate the control circuit 41 and solenoid valve 37 may be the storage battery utilized to provide auto-propulsion for the wheelchair, but in the case where the wheelchair is manually operated, the storage battery 39 may be a small storage battery provided on the wheelchair specifically for the purpose of operating the valve 37.

Referring specifically to the schematic illustration of FIG. 6, the battery is connected to provide a voltage source, typically 12 volts, through a current limiting resistor R1, to the switch 43. In the embodiment illustrated, the switch 43 is a single-pole, double-throw switch which is switched to position 45 to open the solenoid valve 37 and is switched to position 47 to close the valve 37.

A transistor Q1 includes a base and collector terminal which are connected together through a normally-closed relay contact 49. The transistor Q1 is thus maintained in a hard saturated or closed circuit configuration so long as the switch contact 49 is closed. In this hard saturated configuration, current may flow from the positive terminal of the battery 39 through the transistor Q1 to a silicon controlled rectifier CR1. The silicon controlled rectifier CR1 is gated by current flowing through the resistor R1 when the switch 43 is momentarily placed in position 45. The silicon controlled rectifier CR1, once gated, supplies current to the solenoid valve 37 and additionally supplies current through a limiting resistor R4 to a light emitting diode CR4 which is utilized to notify the operator that the valve 37 is open. Other warning devices, such as a buzzer, may be utilized in place of the light emitting diode CR4.

Once the silicon controlled rectifier CR1 has been gated, a return of the switch pole 43 to its neutral position, as shown in FIG. 6, will not affect operation of the solenoid valve 37, since the silicon controlled rectifier CR1 will continue to conduct so long as current is supplied between its anode and cathode.

When the switch 43 is momentarily moved to position 47, current from the battery 39 through the limiting resistor R1 will gate a silicon controlled rectifier CR2, permitting current to flow through a limiting resistor R5 and the energizing coil K1 for the relay contacts 49. This current will open the relay contacts 49, to open the base-to-collector circuit of the transistor Q1, prohibiting current flow to the solenoid valve 37, thus closing this valve 37. After the valve 37 is open, the switch 43 may be released and allowed to return to its neutral position as shown in FIG. 6. When this occurs, current through the relay coil K1 will cease and the relay contacts 49 will return to their normally closed position to saturate the transistor Q1. The silicon controlled rectifier CR1 will prohibit current flow to the solenoid valve 37 until the switch is again moved to position 45.

A capacitor C1 is utilized to maintain current flow through the coil K1 during a short period of time after contact between the switch pole 43 and terminal 47 ceases, in order to assure that the relay contacts 49 open for a sufficient period of time to deenergize the solenoid 37. A diode CR3 is utilized to shunt current generated by the collapsing field within the solenoid 37 upon deenergization. A resistor R2 in parallel with a capacitor C2 are utilized to protect the gate of the silicon controlled rectifier CR2 from spurious conducted and radiated transients which might inadvertently gate the silicon rectifier CR2. In a similar manner, a parallel combination of a resistor R3 and capacitor C3 are utilized to protect the gate of the silicon controlled rectifier CR1 from spurious signals.

It can be seen from the schematic illustration of FIG. 6 that current through the switch 43 is limited by both the limiting resistor R1 and the current flow through the gating circuits of the silicon controlled rectifiers CR1 and CR2. This current may be maintained at an extremely low level in comparison with the current required to operate the solenoid valve 37, in order to protect the switch operator from shock and fire hazards.

Figure 7:
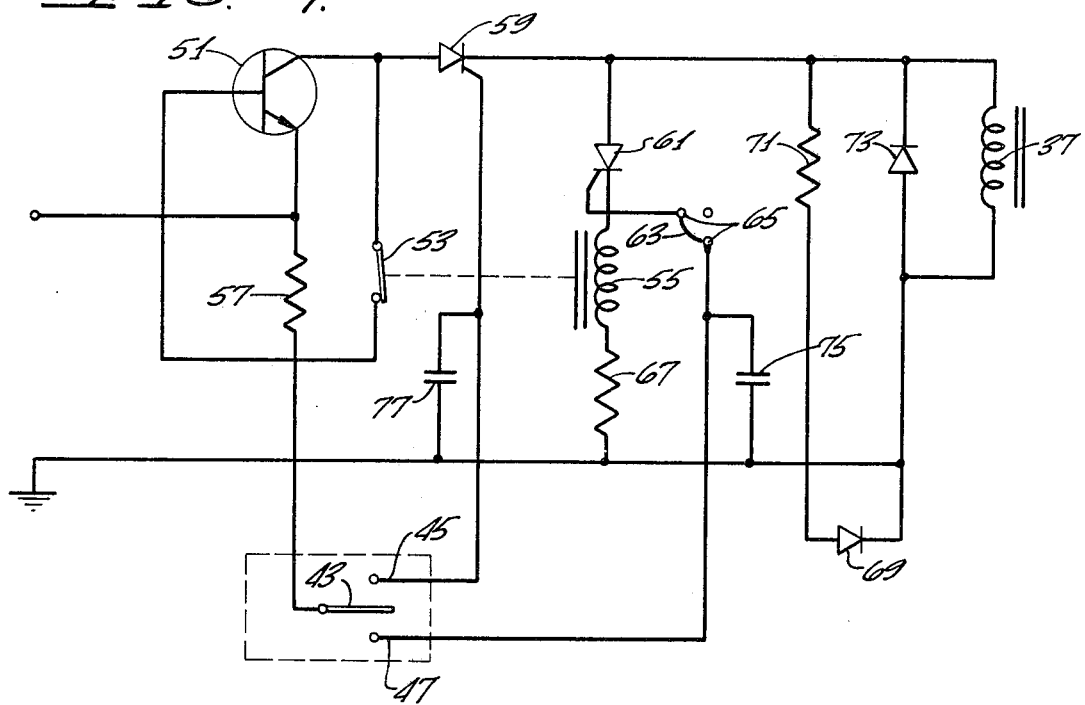
FIG. 7 is a schematic illustration of an alternate embodiment of the electrical circuit utilized to control the solenoid of the apparatus shown in FIG. 5.

Referring now to FIG. 7, an alternate circuit for use as the control circuit 41 in the apparatus on FIG. 5 will be described. The control circuit of FIG. 7 is similar in both construction details and operation to that of FIG. 6, except that some of the elements have been changed or eliminated.

As in the previous embodiment, a transistor 51 is maintained in a hard saturated condition by a connection between its base and collector terminals passing through the normally closed contacts 53 of a relay 55. A momentary operation of the switch 43 to a first terminal 45 provides gating current through a limiting resistor 57 to gate a silicon controlled rectifier 59 for supplying current to the solenoid valve 37. Manipulation of the switch 43 to a second contact 47 provides gating current to a silicon controlled rectifier 61 through a jumper wire 63 and a pair of terminals 65 which permit disconnection of the silicon rectifier 61 from the switch terminal 47. When gated, the silicon controlled rectifier 61 provides current through the coil of relay 55 through a limiting resistor 67. A light emitting diode 69 is utilized to warn the operator that the solenoid valve 37 is open and is energized from the current source through a limiting resistor 71.

A diode 73 is utilized as an inductive current shunt to protect the circuit from currents caused by the collapsing field in the solenoid 37. A capacitor 75 is utilized to protect the gate of the silicon controlled rectifier 61 from spurious signals and a capacitor 77 serves a similar purpose with respect to the gate of the silicon controlled rectifier 59. It can be seen that the circuit of FIG. 7 operates to gate the silicon controlled rectifier 59 when the switch 49 is momentarily connected to the terminal 45, opening the solenoid valve 37. A placement of the switch pole 43 momentarily in contact with the terminal 47 will gate the silicon controlled rectifier 61, if the jumper wire 63 is connected as illustrated in FIG. 7, supplying current through the limiting resistor R3 to the relay 55. This current will open the normally closed contacts 53 to inhibit current flow through the transistor 51, closing the solenoid valve 37. Release of the switch 43 to its neutral position, as shown in FIG. 7, will inhibit current flow through the relay 55, so that the transistor 51 will again saturate. By this time, however, the silicon controlled rectifier 59 has ceased conduction so that a new gating signal from the terminal 45 is required to again open the solenoid valve 37.

Figure 8:
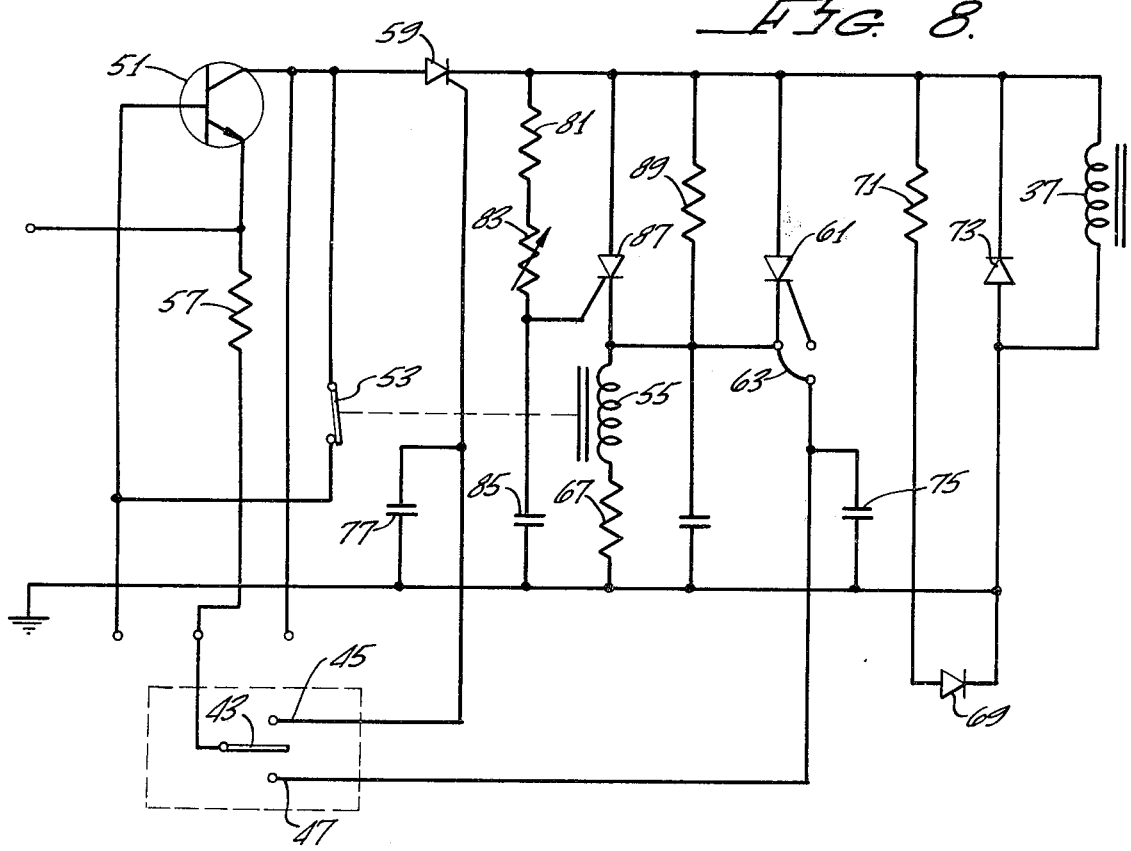
FIG. 8 is a schematic illustration of a second alternate embodiment of a control circuit utilized to control the solenoid in FIG. 5.

Referring now to FIG. 8, a second alternate embodiment for the control circuit 41 of FIG. 5 will be described. In this instance, operation of the circuit elements to open the solenoid valve 37 is identical to operation of the circuit of FIG. 7. Additionally, operation of the switch 43 to close the solenoid valve 37 through the silicon controlled rectifier 61 is identical to operation of the circuit shown in FIG. 7 if the jumper wire 63 is placed in the dotted line position shown in FIG. 8. If, however, the jumper wire 63 is placed in the solid line position shown in FIG. 8, signals from the terminal 47 will not gate the silicon controlled rectifier 61 and will have no effect.

With the jumper wire 63 placed in the position shown in FIG. 8, the circuit operates to automatically close the solenoid valve 37 a predetermined time interval after the valve 37 has been opened. When the silicon controlled rectifier 59 begins to conduct current, current will flow through a fixed resistor 81 and a variable resistor 83 to charge a capacitor 85. The common terminal of the resistor 83 and capacitor 85 are connected to the gating circuit of a silicon controlled rectifier 87 so that a voltage ramp is applied to this gating circuit as the capacitor 85 is charged following energization of the solenoid 37. The silicon controlled rectifier 87 is biased by a resistor 89 which sets the trigger voltage of the silicon controlled rectifier 87. By manipulating the variable resistor 83, the charge rate of the capacitor 85 may be varied so that the time period between an energization of the solenoid 37 and the gating of the biased silicon controlled rectifier 87 may be controlled. Once the voltage on the capacitor 85 has exceeded the gating voltage of the silicon controlled rectifier 87, this rectifier 87 will conduct, opening the normally closed contacts 53 of the relay 55. In a typical installation, the time delay generated by the capacitor 85, silicon controlled rectifier 87, and resistors, 81, 83 and 89 is selected to be variable (through control of the resistor 83) between 30 and 90 seconds. In addition, it can be seen that, through a manipulation of the jumper wire 63, the use of the switch 47 for manually deenergizing the solenoid 37 may be prohibited. Thus, for example, when a tongue switch is used for the switch 43, a single-pole, single-throw switch is all that is required, the solenoid always being deactuated automatically. The circuit of FIG. 8 therefore gives the operator the option of timed deenergization of solenoid 37 with a manual override to prematurely deactuate the solenoid 37, or a simple timed deactuation with the use of a single-pole, single-throw switch, such as a tongue-actuated switch.

What is claimed is:

1. Apparatus for controlling the disposal of urinary waste from a collection receptacle carried by a wheelchair occupant, said receptacle including a drain tube, comprising:
   a valve rigidly connected to said wheelchair and selectively positionable to an open or closed configuration;
   an inlet conduit for said valve connected to said drain tube;
   an outlet conduit for said valve, said outlet conduit extending from said valve to a location beneath said wheelchair; and
   means connected to said valve and extending to a position remote from said valve and proximate said occupant for selectively positioning said valve to said open configuration to permit flow of said waste from said receptacle, through said valve and outlet conduit, onto the floor beneath said wheelchair.

2. Apparatus for controlling the disposal urinary waste as defined in claim 1 wherein said means for selectively positioning said valve comprises:
   a lever mounted on said wheelchair and connected to selectively position said valve, said lever extending to a position proximate said occupant.

3. Apparatus for controlling the disposal of urinary waste as defined in claim 2 wherein said wheelchair includes a footrest, and wherein said valve is connected to the underside of said footrest.

4. Apparatus for controlling the disposal of urinary waste as defined in claim 3 wherein said lever is adapted to permit rotation of said footrest relative said wheelchair.

5. Apparatus for permitting the convenient discharge of waste fluid collected in a receptacle from a wheelchair confined individual, comprising:
   a wheelchair;
   a discharge tube mounted on said wheelchair, fluidly connected to said receptacle and extending to a location beneath said wheelchair;
   means for controlling flow through said discharge tube to permit selective discharge of said waste fluid from said receptacle to said location beneath said wheelchair; and
   means connected to said flow controlling means and extending to a position remote from said flow controlling means and proximate said individual for selectively operating said flow controlling means to discharge said waste fluid to said location beneath said wheelchair.

6. Apparatus for permitting the convenient discharge of waste fluid as defined in claim 5 wherein said flow controlling means comprises a manually actuated valve connected to said discharge tube, and wherein said selectively operating means comprises a lever pivotally mounted on said wheelchair and extending from said valve to a location proximate said individual.

* * * * *